United States Patent [19]

Watkins-Pitchford

[11] Patent Number: 4,743,352

[45] Date of Patent: May 10, 1988

[54] SODIUM ION-SELECTIVE ELECTRODE SYSTEM AND METHOD FOR MAKING AN ION-SELECTIVE ELECTRODE

[75] Inventor: John M. Watkins-Pitchford, Ann Arbor, Mich.

[73] Assignee: The University of Michigan, Ann Arbor, Mich.

[21] Appl. No.: 908,263

[22] Filed: Sep. 17, 1986

[51] Int. Cl.$^4$ .............................................. G01N 27/30
[52] U.S. Cl. .................................... 204/406; 204/418; 427/58
[58] Field of Search ............... 204/418, 1 A, 406, 296; 427/58

[56] References Cited

U.S. PATENT DOCUMENTS

| | | | |
|---|---|---|---|
| 3,103,480 | 9/1963 | Watanabe et al. | 204/195 |
| 3,622,745 | 5/1972 | Cosentino | 128/2 E |
| 3,957,612 | 5/1976 | Niedrach et al. | 204/195 M |
| 4,236,987 | 12/1980 | Schindler et al. | 204/195 M |
| 4,314,895 | 2/1982 | Spaziani et al. | 204/195 M |
| 4,340,457 | 7/1982 | Kater | 204/195 R |
| 4,366,038 | 12/1982 | Kearney et al. | 204/195 M |
| 4,379,041 | 4/1983 | Petranek et al. | 204/415 |
| 4,486,290 | 12/1984 | Cahalan et al. | 204/414 |
| 4,504,368 | 3/1985 | Delton et al. | 204/417 |
| 4,505,800 | 3/1985 | Toner et al. | 204/418 |
| 4,519,973 | 5/1985 | Cahalan et al. | 264/267 |
| 4,565,665 | 1/1986 | Fogt | 264/267 |
| 4,565,666 | 1/1986 | Cahalan et al. | 264/267 |
| 4,568,444 | 2/1986 | Nakamura et al. | 204/412 |

FOREIGN PATENT DOCUMENTS 24571 9/1981 Japan ................................. 204/418

OTHER PUBLICATIONS

O. S. Anderson, "Factors Affecting the Liquid Junction Potential in Electrometric Blood pH Measurement," *Scandinav. J. Clin. & Lab. Investigation*, pp. 205–211, vol. 13, 1961.

O. H. LeBlanc et al., "Polymer Membrane Sensors for Continuous Intracascular Monitoring of Blood pH," *Journal of Applied Physiology*, pp. 644–647, vol. 40, No. 4, Apr. 1976.

D. M. Band et al., "Theory of Potassium Ion Selective Electrode," *Intensive Care Medicine*, pp. 50–52, 1977.

Treasure et al., "A Catheter Tip Potassium-Selective Electrode," *Journal of Medical Engineering and Technology*, pp. 271–273, Sep. 1977.

Band et al., "Relationship between Activity and Concentration of Plasma Potassium," *Analyst*, pp. 426, 251, vol. 103, Mar. 1978.

Cobbe et al., "Continuous Measurement of pH in Central Arteries and Veins," *The Lancet*, pp. 444–445, Sep. 1, 1979.

Bird et al., "Intravascular Complications of Transurethral Resection of the Prostate," pp. 564–565, vol. 54, 1982.

(Continued on next page.)

*Primary Examiner*—G. L. Kaplan
*Attorney, Agent, or Firm*—Rohm & Monsanto

[57] ABSTRACT

A sensor arrangement for monitoring ionic concentrations in fluids uses anion-selective membrane formed of N,N'-dibenzyl-N,N'-diphenyl-1,2-phenylenedioxydiacetamide suspended in an inert carrier, such as PVC having a high molecular weight. The membrane is disposed on a porous ceramic plug which permits wetting of the side of the membrane facing the plug with an internal fluid of the system, such as saline. The other side of the membrane communicates with the fluid to be assayed, which in certain intravenous embodiments may be the blood of a patient. In one embodiment, the system is provided with a reference electrode which is arranged to communicate with the fluid being monitored via a dialysis membrane. High impedance electronic circuitry produces a signal indicative of the ionic concentration in response to a potential appearing across the reference and sensor electrodes. The electronic circuitry has wide range offset and gain controls which are independent of one another, while maintaining the circuitry simple and safe for connection to a patient.

20 Claims, 4 Drawing Sheets

OTHER PUBLICATIONS

Sunderrajan et al., "Posttransurethral Prostatic Resection Hyponatremic Syndrome: Case Report and Review of the Literation," *American Journal of Kidney Diseases*, pp. 80-84, vol. IV, No. 1, Jul. 1984.

Dutsch, et al., "Microprocessor-Controlled ex Vivo Monitoring of Sodium and Potassium Concentrations in Undiluted Urine with Ion-Selective Electrodes," *Anal. Chemistry*, pp. 578-580, vol. 57, 1985.

Fogt et al., "Response of Ion-Selective Field Effect Transistors to Carbon Dioxide and Organic Acids," *Anal. Chem.*, pp. 1995-1998, vol. 57, 1987.

Heuser et al., "Ionic Changes in Brain Ischemia and Alterations Produced by Drugs," *Br. J. Anaesth.*, pp. 23-33, 1985.

Simon et al., "Ion-Selective Electrodes and Their Clinical Application in the Continuous Ion Monitoring," *Annals of the New York Academy of Sciences*, pp. 279-285, vol. 428.

SODIUM ION-SELECTIVE ELECTRODE SYSTEM AND METHOD FOR MAKING AN ION-SELECTIVE ELECTRODE

BACKGROUND OF THE INVENTION

This invention relates generally to systems for monitoring ion concentrations, and more particularly, to a system for monitoring sodium ion concentrations in fluids, including fluids contained within human beings.

Throughout a variety of industries, and particularly in various medical fields, there is a need for simple and economical systems which can monitor accurately the concentration of specific ions in fluids. The need for an economical and accurate system which can monitor the concentration of sodium ions is particularly acute in certain medical procedures, such as during transurethral resection of the prostate (TURP).

It is very common in middle aged and elderly men that the prostate gland enlarges and compresses the urethra so as to impede the passage of urine. It has been suggested that approximately 40% of men over 65 years of age have some difficulty in passing urine. The condition is progressive whereby the continued enlargement of the prostate gland occasionally blocks entirely the urethral passageway. This emergency condition, where the man cannot urinate at all, usually requires resection of some or all of the prostate gland to remove the obstruction. Resection can be achieved either by surgical incision or by the passage of an optical cutting instrument through the urethra to resect the gland from the inside.

TURP has many advantages over transdermal surgery. These include, for example, lower expense and reduced hospital stay, patient acceptability, as well as reduction in mortality associated with the ease of sputum clearance from the chest when coughing is not restricted by a painful incision. In addition, early ambulation is believed to contribute to relatively infrequent venous thrombosis and pulmonary embolism.

TURP is usually performed with a fluid-irrigated endoscope. The requirements of optical clarity and non-conduction of the resecting diathermy current by anything other than the tissue to be cut, demand that a non-conducting, and hence sodium-free irrigating fluid be used. The irrigating fluid, however, may have a hydrostatic pressure sufficient to force it into prostatic venous sinuses which are opened during resection of the gland. On the average, in an uncomplicated transurethral resection, the amount of irrigating fluid absorbed is probably between 100 and 1000 ml. However, in certain situations, patients may absorb more than 10 liters of fluid during TURP, and such patients therefore develop the complete TURP syndrome. Although most of the fluid is absorbed during the TURP procedure itself, an additional amount of the irrigating fluid is absorbed after the procedure during the continuous irrigation of the bladder generally conducted after surgery. The resulting increase in fluid load, hyponatremia and hemolysis, which depends upon the nature of the fluid, produce the TURP syndrome. The clinical features of fluid overload and hyponatremia are seen after the circulation has sustained the overload, and are therefore almost useless for warning of impending catastrophe.

Although there are present in the patient during anesthesia certain symptoms and signs associated with the syndrome, this syndrome stands alone as being so commonly encountered with so little to warn of its danger. The symptoms are difficult to interpret since they are to a large extent dependent upon the anesthesia which is used during TURP. For example, patients who are under the influence of spinal anesthesia will show symptoms of confusion, hypertension, nausea, restlessness, and increased central venous pressure. However, in an unconscious patient, the nausea, disorientation, and restlessness are not seen. In fact, some of the other signs of the syndrome are delayed by assisted ventilation. Thus, increasing systolic and diastolic pressures, and increased central venous pressure, which is usually associated with abdominal distention and tightness, are the only signs apparent in a generally anesthetized patient. These observations of signs of acute circulatory overload, as well as the associated electrolyte disturbance, are insufficient warning systems for the care of a patient who may well be old and frail. Other alternatives which have been proposed, such as the monitoring of changes in transthoracic impedance have been too cumbersome, unreliable, or expensive for routine use.

One known system for detecting hemodilution depends upon the taking of serial samples for estimation of some marker of dilution, such as sodium concentration, hematocrit, or osmolarity, will require very many samples at short intervals if prompt detection of early changes is to be possible. It is clear that there is a need for a continuous method of analysis which allows continuous monitoring of hemodilution. In this regard, the plasma sodium concentration is an excellent marker of dilution because it is a familiar index of hydration to physicians, and also, since its ions are electrically conductive, it cannot be present in any irrigating fluid.

The foregoing is merely illustrative of a specific need in the present state of the art. There is additionally a need to monitor, in medical and other fields, a variety of other ion concentrations, such as $K^+$, $H^+$, and $Ca^+$. The need to monitor such concentrations accurately is present in the manufacture of food and drugs, the brewing industry, the production of fertilizers, the treatment of sewage, and other technical fields.

It is, therefore, an object of this invention to provide a simple and economical system for measuring ionic concentrations.

It is another object of this invention to provide an ion concentration monitoring arrangement which uses membranes rather than field effect transistors.

It is also an object of this invention to provide an arrangement for monitoring the concentration of ions and which can be miniaturized sufficiently for insertion into a living being.

It is additionally an object of this invention to provide a system which can easily be adapted to monitor various types of ionic concentrations.

It is a further object of this invention to provide an ionic concentration monitoring system which can be adapted to be selective and therefore particularly responsive to a particular ion.

It is still another object of this invention to provide an ion concentration monitoring system which does not employ hazardous electrical potentials.

It is a yet further object of this invention to provide an ion sensor which is easy to fabricate.

It is also a further object of this invention to provide a system which reacts quickly to changes in ionic concentration.

It is yet another object of this invention to provide an ionic concentration monitoring system which is electrically stable and has low drift.

SUMMARY OF THE INVENTION

The foregoing and other objects are achieved by this invention which provides an arrangement for monitoring concentration of a predeterminable ion in a fluid, the arrangement having an elongated body with a lumen therein and a porous ceramic member arranged at one end of the elongated body for closing the lumen. An ion-selective membrane is arranged over the outside of the porous ceramic member, and is formed of N,N'-dibenzyl-N,N'-diphenyl-1,2-phenylenedioxydiacetamide suspended in a substantially inert vehicle. In one embodiment, the vehicle is high molecular weight PVC with a plasticizer. In addition, there is provided a sensor electrode which is arranged in the lumen of the elongated body and in the vicinity of the porous ceramic member. In a preferred embodiment, the electrode is formed of silver which is coated with silver chloride.

In embodiments of the invention where it is desired to reduce transportation through the membrane of lipophilic substances, potassium tetraphenylchloroborate is added to the composition of the membrane. Lipophilic substances tend to be transported through the membrane without using the selective carrier, N,N'-dibenzyl-N,N'-diphenyl-1,2-phenyldioxydiacetamide. In this regard, a primary difficulty is raised by the carbon dioxide-hydrogen ion system, which, if permitted to pass freely through the membrane, would cause an undesirable change in charge on the sensing membrane resulting from hydrogen ion charges unrelated to the sodium ions being selectively carried. In addition, this additive appears to reduce the effective electrical impedance of the sensor and thereby improve its susceptibility to electrical interference.

The sensor electrode is formed of silver on which is deposited silver chloride. In a specific illustrative embodiment, wire coated with "Teflon" insulating material is of sufficiently small diameter to fit easily inside a tube which forms the elongated body is cut into lengths about 5 cm longer than the tube. One end of the wire is scraped clean for about 1 cm and the other for about 5 cm, such as by the use of fine grade emery cloth. The longer bare end is immersed in a strong saline solution and a current is passed between it and a solid silver cathode. Gassing is observed on the silver wire, which loses any remaining "Teflon" insulating material. The current is then reversed and limited to current density which deposits silver chloride evenly on the wire as a black or dark brown coating. An excessively high current density results in a useless light-colored coating, while too low a current density takes an unnecesarily long time. Experience with the particular facility being used will enable an operator skilled in the art to select current limiting resistors having values which result in a current density of about 10 mA/cm$^2$ of bare silver. At such current densities, a typical coating is completed in approximately 10 and 15 minutes. The coating should extend right up to the "Teflon" insulating coating.

In a highly advantageous embodiment of the invention, a reference electrode is provided in a reference chamber which communicates with the fluid being monitored via a permeable membrane, such as a dialysis membrane, which may be a cellulose film. The reference electrode is also formed of chloridized silver, as indicated hereinabove with respect to the sensor electrode. In operation, the reference electrode provides a constant potential to a measuring apparatus so that any observed differences with respect to it may be correctly attributed to the sensor.

In one embodiment, the sensor is formed by dip-casting a sodium-selective membrane onto a porous ceramic plug which is wetted on its inside by an internal electrolyte solution containing sodium chloride and on its outside with the fluid to be analyzed. The membrane thus acquires a charge according to the Nernst equation. The internal electrolyte communicates this charge to the silver-silver chloride electrode immersed therein, and formed as indicated hereinabove. Preferably, the electrolyte solution has a temperature coefficient with respect to silver chloride which is opposite to that of the membrane, thereby compensating for temperature effects on the whole sensor.

A specific illustrative sodium-selective membrane constructed in accordance with the invention has the following composition:

| | |
|---|---|
| N,N—dibenzyl-N,N'—diphenyl-1,2-phenylenedioxydiacetamide | 10 mg |
| potassium tetraphenylchloroborate | 0.01 mg |
| PVC (high molecular powder) | 100 mg |
| dioctyl sebisate | 200 mg |
| tetrahydrofuran | 6 g |

The function of the components may be summarized as follows: the polyvinyl chloride is the same material which forms the tube of the elongated body and therefore is a convenient inert vehicle in which to suspend the ion carriage chemistry and to weld it securely to the tube. Rubber membranes of polydimethylsiloxane, which typically are used for anions, can be used for the sodium cation herein, but are not as convenient to work with as PVC. Ion carriage is achieved by N,N'-dibenzyl-N,N'-diphenyl-1,2-diphenlyenedioxydiacetamide. This material is commercially available under the trademark "ETH-157" (owned by Fluka, AG, and available from Fluorochem, Ltd., Glossop, Derbyshire, England). The potassium tetraphenylchloroborate is, as indicated, added to discourage interference by lipophilic substances, the dioctyl sebisate is a plasticizer, and the tetrahydrofuran is a solvent which regulates viscosity and allows mixing and dip-casting. The amounts indicated hereinabove are sufficient to form a batch of approximately between 50 and 100 membranes for indwelling ion sensors.

In accordance with a method aspect of the invention, N,N'-dibenzyl-N,N'-diphenyl-1,2-phenylenedioxydiacetamide is combined with a plasticizer in a substantially airtight container to form a first mixture. Dissolved PVC is added to the first mixture to form a second mixture; the second mixture being evaporated to increase its viscosity. Subsequently, the viscous second mixture is cast onto a porous member to form the ion-selective membrane.

More specifically, the membrane is made by adding the plasticizer to a clean glass weighing pot fitted with an airtight screw top and a magnetic stirring flea. The mixture is stirred after the addition of each ingredient. The ion carrier is added next, then tetraphenylchloroborate. The PVC is weighed in a separate pot with tetrahydrofuran solvent. When dissolved, the PVC is added to the first pot and the resulting mixture is stirred for 6 hours. The solution should be perfectly clear. Haziness is associated with poorly functioning membranes, and overt cloudiness with uselessness. The satisfactory mix is then evaporated slowly at rioom temperature with the lid of the pot supported with a filter paper pad weighted with about 20 grams. The airtight lid is replaced when the now viscous mix will only just flow when tipped.

To dip-cast membranes, a batch of lengths of PVC tubing is prepared of just greater length than the intended final sensor. A porous ceramic plug is inserted into one end of each tube. Preferably, the plug, which may be formed of a different porous material, extends from the tube by about twice the plug diameter. The tube is then given a temporary stiffening wire so that it can be handled with precision more easily. The tube bearing the plug is fit into the membrane mix so that only the plug of porous ceramic material is wetted. The tube is then raised above the liquid surface by about 1 cm where evaporation of the solvent is allowed for approximately 15 seconds before it is removed from the pot and set aside to dry while the rest of the batch is treated similarly. After giving the last one of the batch its first dip, the process is repeated in turn on each of the others until three to five coats have been applied. The tubes are then allowed to dry for at least one day.

When the tubes are dry, they are filled with saline electrolyte, either with fine steel needle tubing or by aspiration after prior extraction of air with saline. Remaining air bubbles are removed by tapping the side of the tube until the porous plug is well wetted. The chloridized silver wire is then introduced so as to end in the vicinity of the plug.

The membranes are next tested by immersion in saline standards of exactly doubling concentrations. Although such doubling causes a variation of total ionic strength of solution, and therefore of molar activity coefficient, the effects of the dilution on aspects other than those of concentration are incorporated into the calibration. The membrane potentials are measured with respect to a calomel reference half-cell and any not achieving about 16 mV or better change in output when moved between standards is disregarded. The better tubes are closed at their open ends with PVC adhesive and silicone rubber. The now closed ends are fitted with Luer-size fittings and electric connectors to allow them to be fitted to standard intravenous equipment. These completed electrodes are kept in sterile saline until shortly before use when they are sterilized by immersion in activated glutaraldehyde for a time recommended by the manufacturer. At completion of the sterilizing period, the excess glutaraldehyde is washed off with sterile saline before the sensor is introduced down an intravenous cannula sited in a patient's vein.

The concentration of internal saline electrolyte is not critical, but immunity from temperature fluctuations may be obtained with about a molar concentration. This results in the partial cancelling of the temperature effect on the membrane by the temperature effect of the contact potential of the silver-silver chloride couple. Although higher concentrations may do even better in this respect, very high concentrations may destroy the membrane. Thus, the specified concentration seems to be a good compromise.

In accordance with a further aspect of the invention, an ion-selective membrane is arranged to have a first side thereof communicate with a fluid to be assayed, and a second side to communicate with a first internal fluid of the system. A sensor electrode is in communication with the first internal fluid, and a reference electrode is arranged to communicate with a second internal fluid of the system. A further membrane, which in certain embodiments may be a dialysis membrane, is arranged to communicate on a first side thereof with the second internal fluid of the system, and on a second side thereof with the fluid being monitored. There is additionally provided a monitoring arrangement having first and second input terminals which are coupled electrically to the sensor and reference electrodes, respectively. The monitoring arrangement produces an output signal which is responsive to a potential across the input terminal, and a gain characteristic and has a voltage offset characteristic which are adjustable independently of one another.

The monitoring arrangement is configured to have a measure of symmetry to achieve useful common mode rejection. Additionally, the arrangement is characterized with high linearity and low battery consumption. A voltage amplifier of floating design works against a complementary amplifier which is arranged essentially as a voltage follower of a predetermined voltage. In one embodiment, a visual indicator, which may be a center-zero meter movement is provided to show fluctuations between the reference and sensor electrodes. Circuitry is included for limiting meter current in a manner which balances the inductive load between the complementary amplifiers, permits adjustment of the relative gains of the amplifiers, and damps parasitic oscillations. The voltage offset characteristic of the monitoring arrangement, as well as the floating aspect of the circuitry, combine to compensate for potentials generated across a fluid junction where the fluid to be assayed combines with a fluid of the reference electrode.

BRIEF DESCRIPTION OF THE DRAWING

Comprehension of the invention is facilitated by reading the following detailed description in conjunction with the annexed drawings, in which.

DETAILED DESCRIPTION

Figure 1:
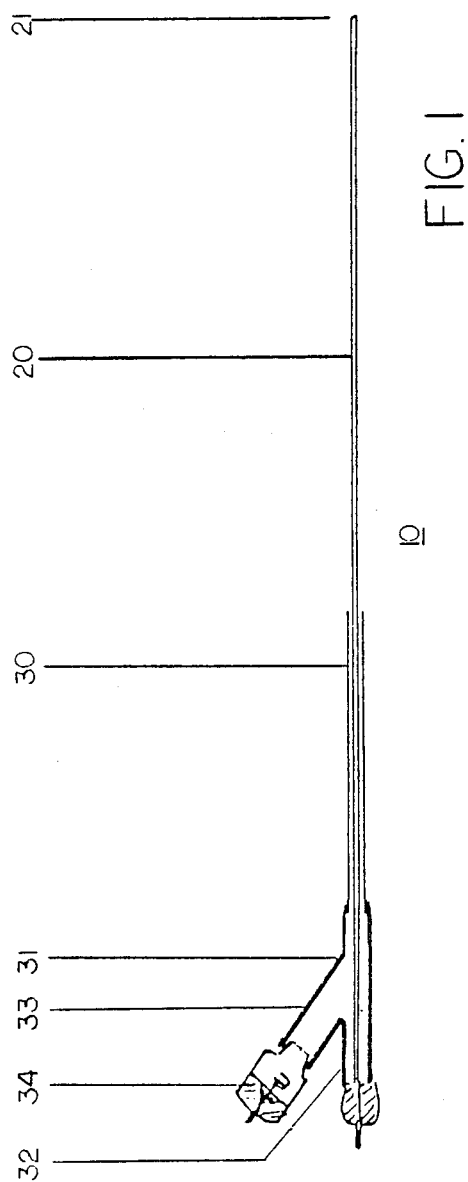
FIG. 1 is a schematic representation of an assembly constructed in accordance with the invention.

FIG. 1 is a schematic representation of an ion concentration monitoring arrangement 10 constructed in accordance with the principles of the invention. Arrangement 10 is provided with a sensor arrangement 20 having an ion sensitive tip 21. In this illustrative embodiment, sensor arrangement 20 is arranged within an intravenous cannula 30 having at a distal end thereof a Y-connector 31. As shown, Y-connector 31 has a first limb 32 on which is provided an electrical termination for sensor arrangement 20, as will be described hereinbelow with respect to FIG. 3. FIG. 1 further shows a second limb 33 of Y-connector 31 in which is provided a reference electrode assembly 34, which will be described hereinbelow.

Figure 2:
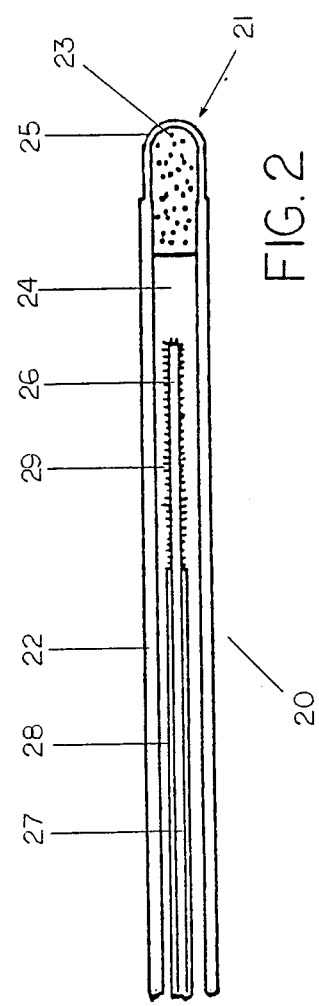
FIG. 2 is a schematic representation of a sensor tip constructed in accordance with the invention and employed in the embodiment of FIG. 1.

FIG. 2 is a schematic representation of the distal portion of sensor arrangement 20 showing certain details of a specific illustrative embodiment of ion-sensitive tip 21. As shown in this figure, a PVC tube 22 is terminated with a porous ceramic plug 23, so as to block and extend beyond a lumen 24 of the PVC tube. Of course, any of several known porous materials can be used in place of the ceramic plug. Porous ceramic plug 23 is covered on an external surface thereof with an ion-selective membrane 25. In this embodiment, ion-selective membrane 25 is formed of N,N'-dibenzyl-N,N'-diphenyl-1,2-phenylenedioxydiacetamide suspended in a vehicle, illustratively PVC with a plasticizer such as dioctyl sebisate. An illustrative method of forming the membrane has been discussed hereinabove.

The sensor tip of the present invention is provided with a sensor electrode 26 which is formed of a silver wire 27 which is covered with a "Teflon" insulation 28. An exposed portion of the silver wire is provided with a coating of silver chloride 29, as described hereinabove. Lumen 24 of the PVC tube is filled with an internal fluid, illustratively a saline solution.

Figure 3:
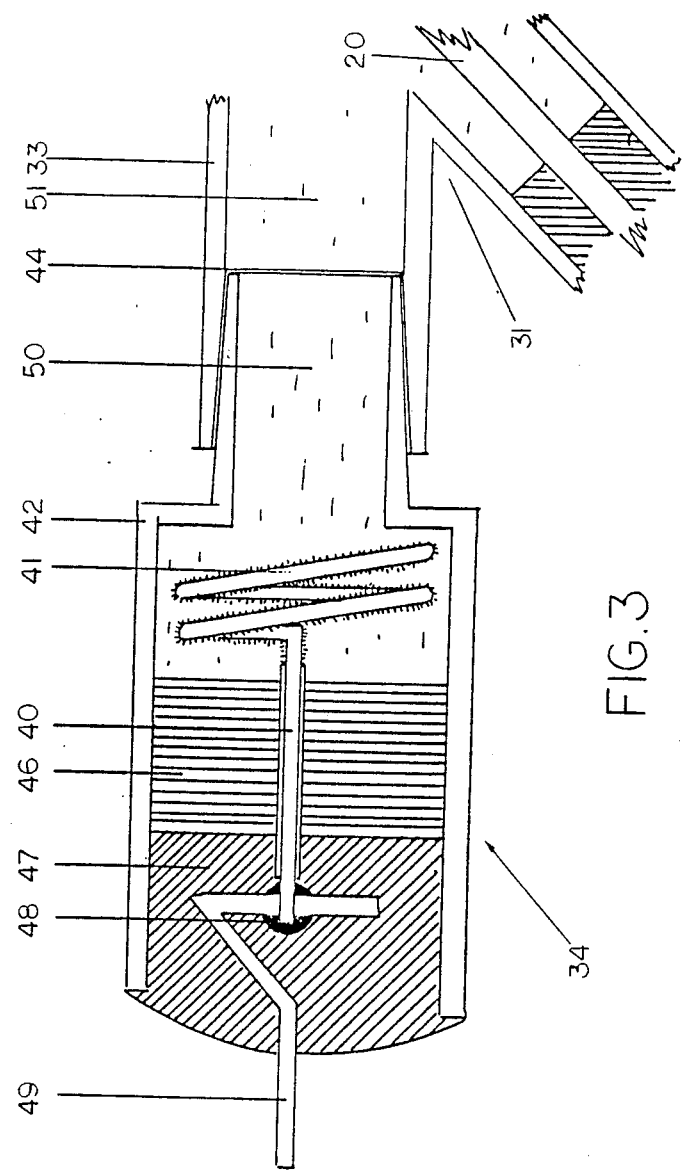
FIG. 3 is a schematic representation of a reference electrode constructed in accordance with the invention and employed in the embodiment of FIG. 1.

FIG. 3 is a schematic representation of the other end of ion-concentration monitoring arrangement 10, showing Y-connector 31 and reference electrode assembly 34 arranged in second limb 33 of the Y-connector. In this embodiment, the reference electrode is a coated silver wire 40 the coating being "Teflon" insulating material, similar to that described hereinabove with respect to FIG. 2. The silver wire is provided with a coating of silver chloride 41 over a portion thereof, which portion is enclosed in a chamber defined in part by an electrode case 42. As shown in the figure, electrode case 42 is provided with a tapered portion 43 which mates with second limb 33 of Y-connector 31. In this embodiment, however, a dialysis membrane 44 is arranged to cover the opening of the tapered portion of the electrode case, and is held in place in the taper.

The other end of the chamber is sealed by a rubber bung 46 which is held in place by an epoxy resin 47. The rubber bung and the epoxy resin are configured in their centers to accommodate the Teflon coated silver wire which is electrically coupled at a solder joint 48 with an electric terminal 49. The reference electrode chamber defined by electrode case 42, dialysis membrane 44, and rubber bung 46 is filled with an electrolyte, which may be a dilute saline solution in one embodiment of the invention.

On the other side of dialysis membrane 44, an electrolyte 51 is arranged which communicates with the internal fluid of the patient (not shown) via the intravenous cannula. The internal fluid of the patient, which may be blood, therefore communicates directly with dialysis membrane 44. The dialysis membrane permits ions to cross therethrough into electrolyte 50, but not blood proteins.

Figure 4:
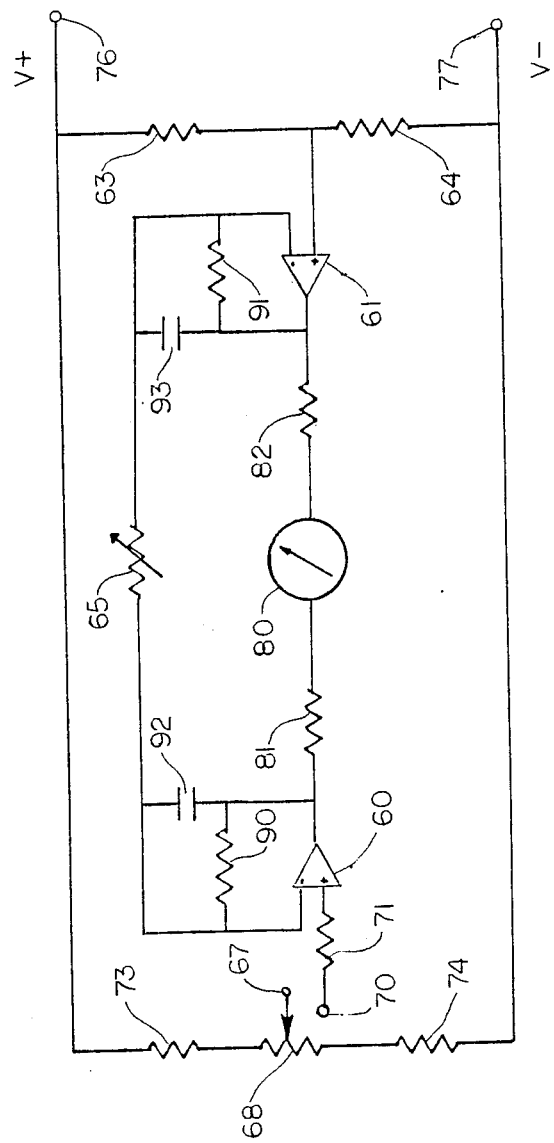
FIG. 4 is a schematic representation of electronic circuitry for providing a visual indication of ionic concentration.

FIG. 4 is a schematic representation of a specific illustrative circuit arrangement constructed in accordance with the invention for producing a signal responsive to a voltage across the reference and sensor electrodes. A fundamental difficulty addressed by the present invention is in the area of data acquisition from the sensors wherein the signal appears as a potential on a nonconducting plastic membrane. Thus, if any current is allowed to flow, the potential and signal disappear. It is therefore essential that the electronic system used with sensors be suitably calibrated to measure electrical potentials, while drawing negligible currents from its input sources. Additionally, the electronics must be simple and reliable and satisfy all electrical safety requirements for patient-connected equipment.

It is evident from FIG. 4 that there is present in the circuitry a measure of symmetry, and such symmetry is useful in achieving relatively high common mode rejection. Further significant features of the circuitry are that gain and offset are widely variable independently of one another, while retaining excellent linearity. Additionally, the specific illustrative embodiment is very efficient in that the rate of battery consumption is quite low.

In the circuit of FIG. 4, amplifier 60 functions as a non-inverting CMOS voltage amplifier of floating design working against a complementary amplifier 61. Amplifier 61 functions substantially as a voltage follower of the potential at the junction of resistors 63 and 64. However, there is additionally a contribution from a gain controller, in the form of a variable resistor 65.

The reference electrode is electrically coupled to an input terminal 67 which, in this embodiment, is the wiper contact terminal of a variable resistor 68. This variable resistor, as well as variable resistor 65, can be of the multiturn cermet type to facilitate adjustment. The sensor electrode is connected electrically to an input terminal 70 which is connected via a resistor 71 to the noninverting input of amplifier 60. Variable resistor 68 is electrically interposed between resistors 73 and 74 which are connected to respective ones of supply terminals 76 and 77. Similarly, resistors 63 and 64 are also connected to respective ones of supply terminals 76 and 77. The circuit is caused to float for offset control by variable resistor 68. In this embodiment, the offset control effected via variable resistor 68 is entirely independent of the gain control effected via variable resistor 65. A visual indicating meter 80 is connected to the output terminal of amplifiers 60 and 61 via respective resistors 81 and 82. The ohm values of resistors 81 and 82 are selected depending upon the maximum safe current which can be passed through meter 80, and preferably are of equal value to one another. These resistors, therefore, serve the dual purpose of limiting meter current, while also insuring that neither amplifier drives a different inductive load in the event that an AC interference signal is applied to both.

Fine tuning of common mode rejection is achieved by adjusting the relative gains of amplifiers 60 and 61. Such individual gains can be adjusted by selection of the values of feedback resistors 90 and 91, and capacitors 92 and 93. Satisfactory results are obtained if resistors 90 and 91 are equal in value to one another and capacitors 92 and 93 are also equal to one another.

Resistor 71, at the input of amplifier 60, serves to damp parasitic oscillations which might otherwise be set up in the input line from the sensor. The value of resistor 71 is rather large, but is relatively small when compared to the high input impedance of amplifier 60.

A practical embodiment of the invention has been constructed using the following components:

| | |
|---|---|
| Resistors 63, 64, 73, and 74 | 220 Kohms |
| Resistors 90 and 91 | 5.2 Mohms |
| Resistors 71, 81, and 82 | 470 Kohms |
| Variable resistor 68 | 20 Kohms, multiturn |
| Variable resistor 65 | 500 Kohms |
| Capacitors 92 and 93 | 0.1 Mfarads, polystyrene miniature |
| Amplifiers 60 and 61 | 7621DCPA |
| Meter 80 | 100-0-100 μamp |
| Battery V+,− | 1.5 V alkaline, AA |

Although the invention has been described in terms of specific embodiments and applications, persons skilled in the art can, in light of this teaching, generate additional embodiments without exceeding the scope or departing from the spirit of the claimed invention. Accordingly, it is to be understood that the drawings and descriptions in this disclosure are preferred to facilitate comprehension of the invention and should not be construed to limit the scope thereof.

What is claimed is:

1. An arrangement for monitoring concentration of sodium ions in a fluid, the arrangement comprising:
   elongated body means having a lumen therein;
   porous ceramic means arranged at one end of said elongated body means for closing said lumen of said elongated body means;
   ion-selective membrane means for covering at least a portion of said porous ceramic means outside of said lumen of said elongated body means, said ion-selective membrane means being formed of N,N'-dibenzyl-N,N'-diphenyl-1,2-phenylenedioxydiacetamide suspended in a substantially inert vehicle; and
   sensor electrode means arranged in said lumen of said elongated body means and arranged in the vicinity of said porous ceramic means for detecting a potential.

2. The arrangement of claim 1 wherein said ion-selective membrane means is further formed of potassium tetraphenylchloro borate for reducing transportation through said ion-selective membrane means of lipophilic substances from the fluid.

3. The arrangement of claim 1 wherein said sensor electrode means is formed of silver on which is deposited silver chloride.

4. The arrangement of claim 1 wherein there is further provided reference electrode means arranged in a chamber.

5. The arrangement of claim 4 wherein there is further provided dialysis membrane means arranged to separate said chamber of said reference electrode means from the fluid.

6. The arrangement of claim 4 wherein said reference electrode means is formed of silver on which is deposited silver chloride.

7. The arrangement of claim 4 wherein there is further provided circuit means comprising:
   a reference input terminal for communicating electrically with said reference electrode means;
   a sensor input terminal for communicating electrically with said sensor electrode means; and
   indicator means for indicating a value responsive to a potential across said reference input terminal and said sensor input terminal.

8. A method of forming an ion-selective membrane, the method comprising the steps of:
   combining N,N'-dibenzyl-N,N'-diphenyl-1,2-phenylenedioxydiacetamide with a plasticizer in a substantially airtight container to form a mixture;
   adding dissolved PVC to said first mixture to form a second mixture;
   evaporating said second mixture to increase its viscosity; and
   casting said viscous second mixture onto a porous member to form the ion-selective membrane.

9. The method of claim 8 wherein said step of combining further comprises the step of further combining tetraphenylchloroborate into said first mixture.

10. The method of claim 8 wherein said step of adding dissolved PVC comprises the further step of dissolving a PVC powder in tetrahydrofuran to form said dissolved PVC.

11. The method of claim 10 wherein after said step of adding dissolved PVC there is provided the further step of stirring said second mixture.

12. The method of claim 8 wherein prior to said step of casting there is provided the further step of affixing said porous member to a sensor tube having a lumen therein.

13. The method of claim 12 wherein said step of casting comprises the step of dipping said porous member affixed to said sensor tube in said viscous second mixture to form a first membrane layer.

14. The method of claim 13 wherein said step of casting comprises the further steps of:
   drying said first membrane layer; and
   dipping said porous member affixed to said tube in said viscous second mixture to form a second membrane layer overlying said first membrane layer.

15. A system for monitoring sodium ion concentration in a fluid, the system comprising:
   a sodium-ion-selective membrane having a first side for communicating with the fluid and a second side for communicating with a first internal fluid of the system, said sodium-ion-selective membrane being formed of N,N'-dibenzyl-N,N'-diphenyl-1,2-phenylenedioxydiacetamide suspended in an inert carrier;
   a sensor electrode for communicating with said first internal fluid;
   a reference electrode for communicating with a second internal fluid of the system;
   further membrane means having a first side for communicating with said second internal fluid of the system and a second side for communicating with the fluid being monitored; and
   monitoring means having first and second input terminals for communicating electrically with said sensor and said reference electrodes, respectively, and for producing an output signal responsive to a potential across said first and second input terminals, said monitoring means having a gain characteristic and a voltage offset characteristic, said characteristics each being adjustable independently of one another.

16. The system of claim 15 wherein said monitoring means further comprises:
   first and second amplifier means each having an output terminal and inverting and noninverting input terminals; and
   a gain-adjustment circuit coupled to said output terminals and said inverting input terminals of said first and second amplifier means, whereby said output signal is produced across said output terminals of said first and second amplifier means.

17. The system of claim 16 wherein there is further provided offset adjustment means for adjusting said offset characteristic of said monitoring means, said reference electrode being electrically coupled to said output adjustment means, and said sensor electrode being electrically coupled to said noninverting input terminal of said first amplifier means.

18. The system of claim 17 wherein there is further provided oscillation damper means coupled to said noninverting input of said first amplifier means.

19. The system of claim 16 wherein there is further provided indicator means for providing a visual indication of said output signal, coupled to said output terminals of said first and second amplifier means.

20. The system of claim 16 wherein there is further provided voltage divider means for applying a predetermined voltage to said noninverting input terminal of said second amplifier means.

* * * * *